United States Patent [19]

Spencer

[11] Patent Number: 4,768,373
[45] Date of Patent: Sep. 6, 1988

[54] CORROSION AND EROSION SENSOR

[75] Inventor: Larry K. Spencer, Dallas, Tex.

[73] Assignee: Sigma Enterprises, Inc., Dallas, Tex.

[21] Appl. No.: 34,072

[22] Filed: Apr. 2, 1987

[51] Int. Cl.⁴ ............................................ G01N 17/00
[52] U.S. Cl. ...................................................... 73/86
[58] Field of Search ................ 73/86; 137/67; 116/70; 138/36; 29/407

[56] References Cited

U.S. PATENT DOCUMENTS

| | | | |
|---|---|---|---|
| 2,763,534 | 9/1956 | Campbell | 73/86 |
| 3,630,216 | 12/1971 | Kelly | 137/67 |
| 4,389,880 | 6/1983 | Robinet | 73/86 |

OTHER PUBLICATIONS

Otis Surface Safety Equipment and Systems Type Pe Otis Erosion Monitor Pilot, p. 58.
Baker CAC Pilots, Relays and Components-Sand Probe Assembly.
HLR Controls, Inc., Sand Probe Assembly Part No. 7620.
Sigma Enterprises, Inc., Sand Probe Indicator 29 SP 24 dated 12-19-84.

*Primary Examiner*—Stewart J. Levy
*Assistant Examiner*—Robert R. Raevis
*Attorney, Agent, or Firm*—Crutsinger & Booth

[57] ABSTRACT

A sensing probe having a hollow tube for disposition in a flow stream is provided with an internal stiffening rod. A volume between the stiffening rod and the inner surface of the tube communicates with an open end of the sensing probe. In one embodiment, oppositely directed spiral grooves are formed in the surface of the stiffening rod to define the volume. A method of manufacturing the sensing probe includes first inserting a stiffening rod into a tube and then turning the tube to a desired wall thickness.

20 Claims, 1 Drawing Sheet

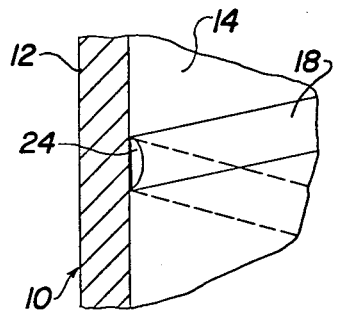
FIG. 3
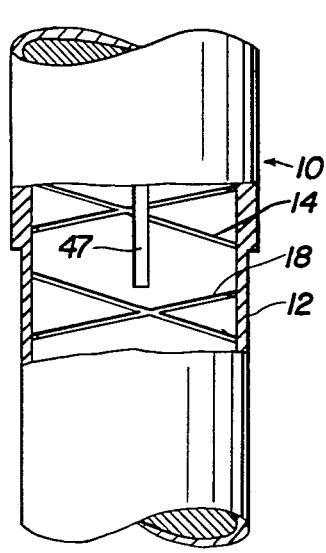
FIG. 2
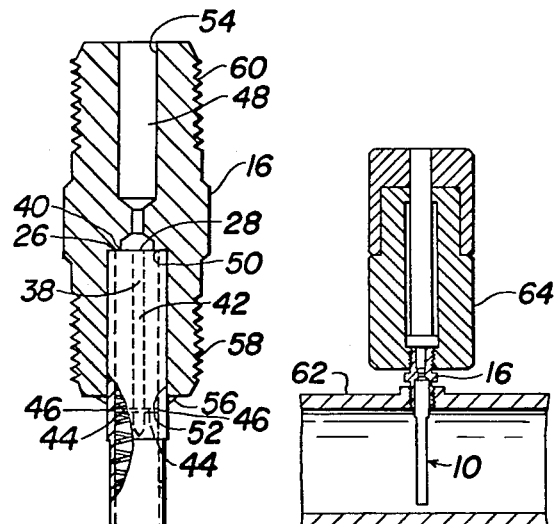
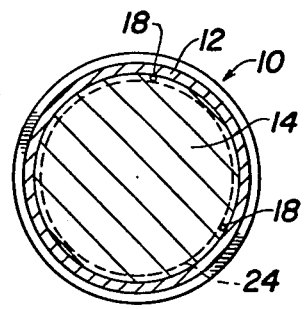
FIG. 5
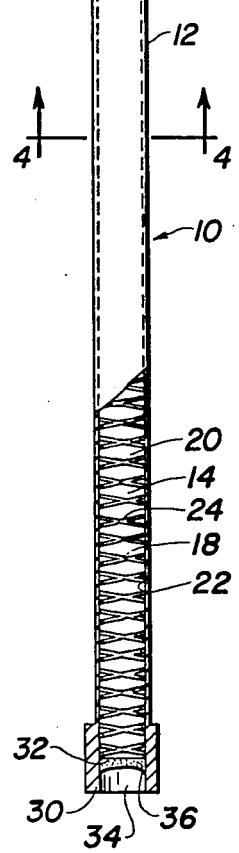
FIG. 4
FIG. 1

CORROSION AND EROSION SENSOR

The invention relates generally to corrosion and erosion sensors for pipelines transmitting fluids and more particularly concerns a corrosion resistant, thin walled, closed end tubular sensing probe which may be suspended in a flow stream to act as a sacrificial corrosion or erosion sensor.

Sensing probes such as the sensing probe disclosed in Kelly U.S. Pat. No. 3,630,216 are known. Sensing probes, which may also be called sand probes, also include Otis Nos. 70P209, 70P225 and 70P236, Baker CAC Nos. 877-47, 877-64 and 877-65, and HLR Controls No. 7620. Outer Continental Shelf Order No. 5 of the U.S.G.S. permits the use of sand probes in erosion control programs. Typically, these probes have an elongated corrosion resistant metallic or plastic tubular member closed at one end and provided with a coupling member at the other end through which the bore of the tubular member communicates to a pressure sensitive indicator. The material and the wall thickness of the tubular member may be selected for the particular application. The material selected is often the same material used for the pipeline. The tubular member is suspended in the flow stream of a pipeline to act as a sacrificial sensor. Corrosive, caustic, acid or alkali fluid within the pipeline may act upon and corrode the tubular member. Similarly, particulate matter such as sand suspended in fluid flowing through the pipeline may impinge upon and erode the tubular member. The material and the wall thickness of the tubular member may be selected so that the corrosive and erosive effects of the fluid will breach the wall of the tubular member before the same corrosive and erosive effects damage or break components of the pipeline. When the tubing wall of the probe is penetrated by any means such as impingement erosion caused by abrasive fluid flow, pressure entering the bore of the probe tubing is transferred to the pressure sensitive valve or indicator, which may operate an alarm system.

A specific usage in oil field service is to sense excessive sand production into a petroleum product flowstream that can lead to erosion failure of production equipment. High sand content fluids erode production flow conduits at a greater rate than do low sand content fluids. A thin-walled sand probe is designed to erode and fail prior to the thick-walled production equipment, thereby providing an alarm signal or equipment shutdown reaction prior to equipment failure. This characteristic has resulted in regulatory acceptance of sand probes as an economical means of monitoring erosion in oil field production operations.

Problems associated with the manufacture and practical application of sand probes are based in the fragile construction of the probes. The thin walls are easily flattened, bent, and broken. Fabrication is difficult for thin walled tubes, and minimum wall thicknesses may be determined by fabrication limitations rather than actual field requirements.

High pressures that envelop the outside of the sand probe impart collapse forces on the thin walled tube, limiting its service pressure. The limited resistance of a thin walled sand probe to physical force and pressure force failure is decreased as erosion thins the wall. As the tubing wall is eroded, it becomes more susceptible to collapse forces. Any flattening or bending of the fragile tube dramatically affects its collapse resistance and its ability to remain extended into the flowstream. The outside diameter of the sand probe is limited to very small diameter (in the range of ⅜", 9.5 mm) to withstand collapse pressures.

The reach or length of the small diameter, thin walled tube is limited because flow of viscous fluids such as those produced in petroleum applications can flex and bend the tube to a position parallel to the pipe wall, thereby reducing its effectiveness. Flexure can also cause breakage of the tube producing false alars in the erosion monitoring system.

Flexure work hardening of fragile tubes induces premature failure, and these flexure forces are additive to the collapse forces and stress risers at the base of the tube attachment to its threaded adapter. These undesirable concentrations of abuse are concentrated at a point that is often a zone of weld attachment of the probe tube to its threaded adapter. This attachment zone is therefore a common failure zone.

Accordingly, an object of this invention is to increase the physical strength and pressure capabilities of a sand probe to enhance the likelihood that the probe can perform its intended function by minimizing false alarms and premature failures.

A further object of this invention is to more easily, accurately and economically fabricate a sensing probe.

An even further object of this invention is to provide thin-wall sensing probes usable in higher pressure applications.

SUMMARY OF THE INVENTION

A sensing probe having a hollow tube for disposition in a flow stream is provided with an internal stiffening rod. A volume between the stiffening rod and the inner surface of the tube communicates with an open end of the sensing probe. In one embodiment, oppositely directed spiral grooves are formed in the surface of the stiffening rod to define the volume. A method of manufacturing the sensing probe includes first inserting a stiffening rod into a tube and then turning the tube to a desired wall thickness.

BRIEF DESCRIPTION OF THE DRAWINGS

Other objects and advantages of the invention will become apparent upon reading the following detailed description and upon reference to the drawing in which:

FIG. 1 is a longitudinal, partially cutaway and partially sectional view of the sensing probe of the invention;

FIG. 2 is an enlarged view of a portion an alternative embodiment of the sensing probe of FIG. 1;

FIG. 3 is an enlarged view of a portion of the sensing probe of FIGS. 1 and 2;

FIG. 4 is a transverse sectional view of the sens ng probe along line 4—4 of FIG. 1, and FIG. 5 is a partial sectional view of the sensing probe of FIG. 1 in its intended environment.

While the invention will be described in connection with a preferred embodiment, it will be understood that the description is not intended to limit the invention to that embodiment. On the contrary, the description is intended to cover all alternatives, modifications and equivalents as may be included within the spirit and scope of the invention as defined by the appended claims.

DETAILED DESCRIPTION OF THE INVENTION

Turning first to FIGS. 1, 2, 3 and 4, there is shown a sensing probe 10 including a thin-wall hollow tube 12, a longitudinally continuous stiffening rod 14 within the tube 12 and a threaded coupling 16 at a first end of the tube 12. Two oppositely directed, intersecting spiral grooves 18 are formed in the outer cylindrical surface 20 of the rod 14. The multiple intersections of the grooves 18 provide multiple fluid paths along the surface 20 within the dimensional envelope of the rod 14 as the ungrooved portions of the surface 20 engage the inner surface 22 of the tube 12. The grooved portions of the surface 20 of the rod 14 together with the inner surface 22 of the tube 12 define a continuous volume 24 along the length of the tube 12 and the rod 14, which volume 24 communicates to the first end 26 of the tube 12 and the first end 28 of the rod 14, which first ends 26 and 28 are both within the threaded coupling 16.

Alternatively, a single spiral groove 18 may be provided in the surface 20 of the rod 14, either alone or in conjunction with one or more axial grooves, not shown, in the surface 20. As will be apparent, other grooves may also be used.

A passage 38 is formed to connect the grooves 18 in the surface 20 of the rod 14 to the face 40 of the first end 28 of the rod 14. Preferably this passage 38 in an axial passage 42 drilled into the face 40 and intersected by a transverse passage 44 drilled through the rod 14 so that the ends 46 of the transverse passage 44 lie within the grooves 18 formed in the surface 20 of the rod 14 Alternatively, an external passage, preferably axial, such as a flat or an axial groove 47 may be ground or otherwise formed into the surface 20 of the rod 14 and the face 40 of the first end 28 of the rod 14. The axial groove 47 may be deeper than the spiral grooves 18.

The second end 30 of the tube 12 is closed. The second end 30 of the tube 12 extends slightly beyond the second end 32 of the rod 14, defining a recess 34 within the second end 30 of the tube 12. Weld metal 36 is deposited within the recess 34 to both seal the second end 30 of the tube 12 and to fix the rod 14 to the tube 12. The second end 30 of the tube 12 and the weld metal 36 may be ground smooth if desired.

The threaded coupling 16 includes a passage 48 therethrough containing within a first end 52 of the passage 48 the first end 26 of the tube 12. Preferably, the first end 28 of the rod 14 is flush with the first end 26 of the tube 12 to abut a shoulder 50 within the passage 48. Alternatively, the first end 26 of the tube 12 extends beyond the first end 28 of the rod 14 to abut the shoulder 50. The passage 38 within the first end 28 of the rod 14 communicates the grooves 18 with the passage 48 of the coupling 16 beyond the shoulder 50 and with the exterior of the coupling 16 at a second end 54 of the passage 48. The tube 12 is fixed and sealed to the coupling by weld metal 56 deposited about the tube 12 at the surface of the coupling 16. The depth of the shoulder 50 exceeds the depth of the axial passage 42 within the rod 16 within the passage 48 of the coupling 16, so that the transverse passage 44 intersects the grooves 18 beyond the zone where the weld metal 56 is deposited, insuring communication in the event that the welding operation partially blocks the grooves 18 in the weld zone. As shown in FIG. 5, means suct as external threads 58 and 60 are provided on the coupling for securing the sensing probe 10 respectively to the pipeline 62 and to a suitable indicator 64, such as a Sigma Enterprises, Inc. 29SP24 Sand Probe Indicator.

Both the wall thickness and the material of the tube 12 may be selected for the specific application of the sensing probe 10. The incorporation of the rod 14 into the tube 12 allows the wall thickness of the tube 12 to be reduced at any subsequent point in the assembly process. A sensing probe may commonly use 0.035", 0.9 mm wall thickness, 0.375", 9.5 mm outside diameter 316 stainless steel tubing for the tube 12, although sensing probes for use in large pipelines may be 3", 76 mm or more in outside diameter. The tube 12 may then be turned on a lathe or ground to a wall thickness as small as 0.010", 25 mm or even 0.005", 0.13 mm along a substantial portion of its length preferably excluding the first end 26 and second end 30 of the tube 12, which ends 26 and 30 are preferably left at their full original diameters in the zones of the weld metal 56 and 36, respectively. The first end 26 may be inserted into a 0.375", 9.5 mm diameter opening in the coupling 16 either before or after the tube 12 is turned. The turning on a lathe of the tube 12 may even be deferred until after the sensing probe 10 is otherwise complete. Alternatively, a completed sensing probe 10 which has already been turned down to a specific wall thickness of the tube 12 may later be further turned to a smaller wall thickness.

The spiral grooves 18 may be formed to a typical width of 0.020", 0.5 mm and a typical depth of 0.010", 0.25 mm at a typical pitch of 0.125", 3.2 mm.

Thus, it is apparent that there has been provided, in accordance with the invention, a corrosion and erosion sensor that fully satisfies the objects, aims and advantages set forth above. While the invention has been described in conjunction with a specific embodiment thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims.

What is claimed is:

1. A sensing probe comprising a tubular member and a longitudinally continuous rod within the tubular member, the outer cylindrical surface of the rod directly contacting the inner surface of the tubular member in structurally supportive engagement with the tubular member, and the surface of the rod and the inner surface of the tubular member defining a volume therebetween which is fluidly communicated with an open first end of the tubular member whereby the physical strength and pressure capabilities of the probe are enhanced.

2. The sensing probe of claim 1 wherein the surface of the rod includes a continuous groove along a substantial portion of the length of the rod.

3. The sensing probe of claim 1 wherein the surface of the rod includes two intersecting, oppositely directed spiral grooves along a substantial portion of the length of the rod.

4. The sensing probe of claim 1 wherein the surface of the rod includes a spiral groove along a substantial portion of the length of the rod.

5. The sensing probe of claim 4 wherein an internal path within the rod fluidly communicates the first end of the tubular member with the groove on the surface of the rod.

6. The sensing probe of claim 4 wherein an axial passage in the outer cylindrical surface of the rod fluidly communicates the first end of the tubular member with the groove in the surface of the rod.

7. The sensing probe of claim 4 further comprising a coupling member fixed to the first end of the tubular member, the coupling member including a passage fluidly communicating the volume and the exterior of the coupling member.

8. The sensing probe of claim 7 wherein the rod bears against an internal shoulder of the coupling member.

9. The sensing probe of claim 1 wherein the second end of the tubular member is closed.

10. The sensing probe of claim 9 wherein the second end of the rod is recessed within the second end of the tubular member and the second end of the tubular member is closed by weld metal fixing the second end of the rod to the inner surface of the tubular member.

11. A corrosion and erosion monitor comprising:
a tubular member and a longitudinally continuous rod within the tubular member, the outer cylindrical surface of the rod both intermittently and directly contacting the inner surface of the tubular member in a structurally supportive engagement with the tubular member and the surface of the rod and the inner surface of the tubular member defining a volume therebetween which is adapted for fluid communication with a means for responding to increased pressure within the volume, whereby the physical strength and pressure capabilities of the monitor are enhanced.

12. A method of manufacturing a sensing probe, comprising the steps of:
(a) inserting a longitudinally continuous rod into both intermittent and direct structurally supporting engagement with the inner surface of a tube so that the outer cylindrical surface of the rod and the inner surface of the tube define a volume extending substantially along the entire length of the tube which volume communicates with a first end of the tube;
(b) after the step of inserting the rod, reducing the wall thickness of the tube;
(c) sealing a second end of the tube; and
(d) providing the first end of said tube with means for coupling including a path fluidly communicating the volume with the exterior of the probe.

13. The method of claim 12 further comprising the step of fixing the tube to the rod after the step of inserting the rod and before the step of reducing the wall thickness of the tube.

14. The method of claim 12 wherein the rod is inserted into the tube so that an end of the rod is recessed within the second end of the tube and the second end of the tube is sealed by sealingly welding the end of the rod to the interior surface of the tube.

15. The method of claim 12 further comprising the step of forming a continuous groove in the surface of the rod substantially along the length of the rod before inserting the rod into the tube.

16. The method of claim 15 further comprising the step of forming two oppositely directed continuous spiral grooves in the surface of the rod substantially along the length of the rod before inserting the rod into the tube.

17. The method of claim 15 wherein the step of providing a means for coupling includes:
(a) inserting the first end, of the tube into an opening in a coupling element so that the first end of the rod bears against an internal shoulder of the coupling element; and
(b) seal welding the coupling element to the tube around the outer surface of the tube.

18. The method of claim 17 further including the step of drilling an axial passage into the first end of the rod and drilling a nonaxial passage into the rod to intersect the axial passage to fluidly communicate the first end of the rod with a groove in the outer surface of the rod between the ends of the rod.

19. The method of claim 17 further including the step of forming an axial passage into the outer cylindrical surface of the rod adjacnet an end of the rod, the axial passage being deeper than the groove in the surface of the rod and the axial passage fluidly communicating the groove with the end of the rod.

20. A method of manufacturing a sensing probe, comprising the steps of:
(a) forming two oppositely directed continuous spiral grooves in the outer cylindrical surface of a longitudinally continuous rod substantially along the length of the rod;
(b) forming a passage interconnecting one of the grooves with a first end of the rod;
(c) inserting the rod into a direct structurally supportive engagement with the inner surface of a tube so that the first end of the rod is adjacent a first end of the tube and a second end of the rod is recessed within a second of the tube;
(d) sealingly welding the second end of the rod to the interior of the tube adjacent the second end of the tube;
(e) after the step of inserting the rod, reducing the wall thickness of the tube along a substantial portion of the length of the tube;
(f) after the step of inserting the rod, inserting the first end of the tube into a first end of a passage through a coupling element so that the first end of the rod abuts against an internal shoulder of the coupling element and a second end of the passage of the coupling element is fluidly communicated with the groove of the rod; and
(g) seal welding the tube to the coupling element adjacent the first end of the passage of the coupling element.

* * * * *

UNITED STATES PATENT AND TRADEMARK OFFICE
CERTIFICATE OF CORRECTION

PATENT NO. :   4,768,373
DATED      :   September 6, 1988
INVENTOR(S) :  Larry K. Spencer It is certified that error appears in the above-identified patent and that said Letters Patent is hereby corrected as shown below:

Column 2, line 11, change "alars" to --alarms--;

Column 3, line 28, change "38 in an" to --38 is an--;

Column 6, line 24, change "adjacnet" to --adjacent--.

Signed and Sealed this

Twenty-first Day of February, 1989

*Attest:*

DONALD J. QUIGG

*Attesting Officer*    *Commissioner of Patents and Trademarks*